(12) United States Patent
Minami et al.

(10) Patent No.: US 8,516,879 B2
(45) Date of Patent: Aug. 27, 2013

(54) GAS SENSOR OUTPUT BASE SUPPORTING A CIRCUIT BOARD

(75) Inventors: Hidekazu Minami, Kasugai (JP); Shingo Yoshida, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 409 days.

(21) Appl. No.: 12/882,818

(22) Filed: Sep. 15, 2010

(65) Prior Publication Data

US 2011/0061443 A1    Mar. 17, 2011

(30) Foreign Application Priority Data

Sep. 17, 2009  (JP) .................. 2009-215878

(51) Int. Cl.
*G01D 11/00* (2006.01)
*G01D 11/26* (2006.01)

(52) U.S. Cl.
USPC ............................. 73/23.2; 73/431

(58) Field of Classification Search
USPC ................................. 73/23.31, 431
See application file for complete search history.

(56) References Cited

U.S. PATENT DOCUMENTS

| | | | |
|---|---|---|---|
| 6,082,176 A | | 7/2000 | Kondo et al. |
| 6,892,565 B2* | | 5/2005 | Sato et al. ............... 73/24.01 |
| 7,758,378 B2* | | 7/2010 | Yoshida et al. ............... 439/587 |
| 2008/0282771 A1* | | 11/2008 | Hamatani et al. ............. 73/23.31 |
| 2012/0164850 A1* | | 6/2012 | Kobayashi et al. ............. 439/55 |
| 2012/0260720 A1* | | 10/2012 | Yoshida et al. ............. 73/31.05 |

FOREIGN PATENT DOCUMENTS

| | | |
|---|---|---|
| JP | 10-270602 A | 10/1998 |
| JP | 11-072478 A | 3/1999 |
| JP | 2005-093905 A | 4/2005 |
| JP | 2009-121975 A | 6/2009 |
| JP | 2009-192486 A | 8/2009 |

* cited by examiner

*Primary Examiner* — Lisa Caputo
*Assistant Examiner* — Punam Roy
(74) *Attorney, Agent, or Firm* — Sughrue Mion, PLLC

(57) ABSTRACT

A gas sensor comprises a gas sensing element, a storage medium to store individual information prepared individually for the sensing element for use in control of the sensing element, and a circuit board supporting the storage medium mounted on the circuit board. A seal portion of a resin covers the circuit board liquid-tightly. An output base includes a mount surface facing to the circuit board. A terminal portion extending through the mount surface is connected with the circuit board and arranged to deliver the individual information through the circuit board. The output base further includes a support projection projecting from the mount surface and including a support surface supporting the circuit board.

9 Claims, 11 Drawing Sheets

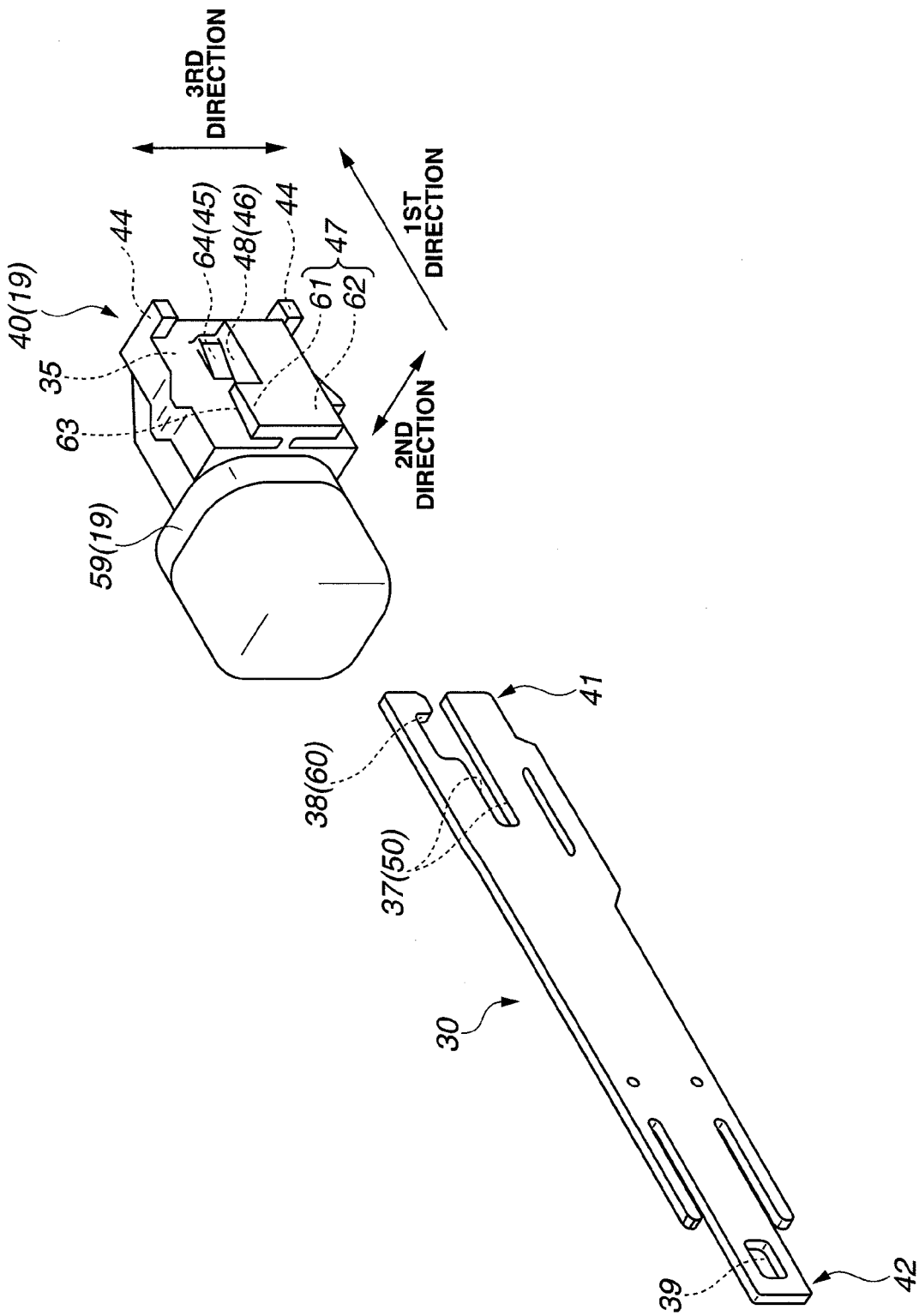

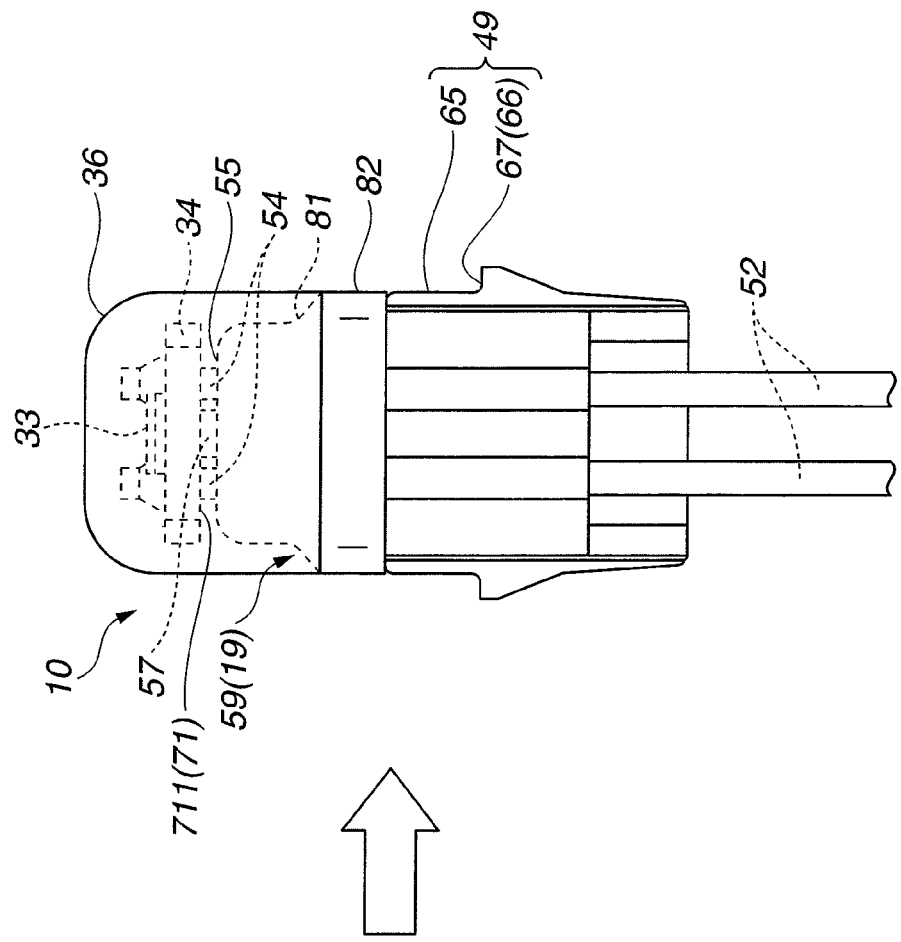
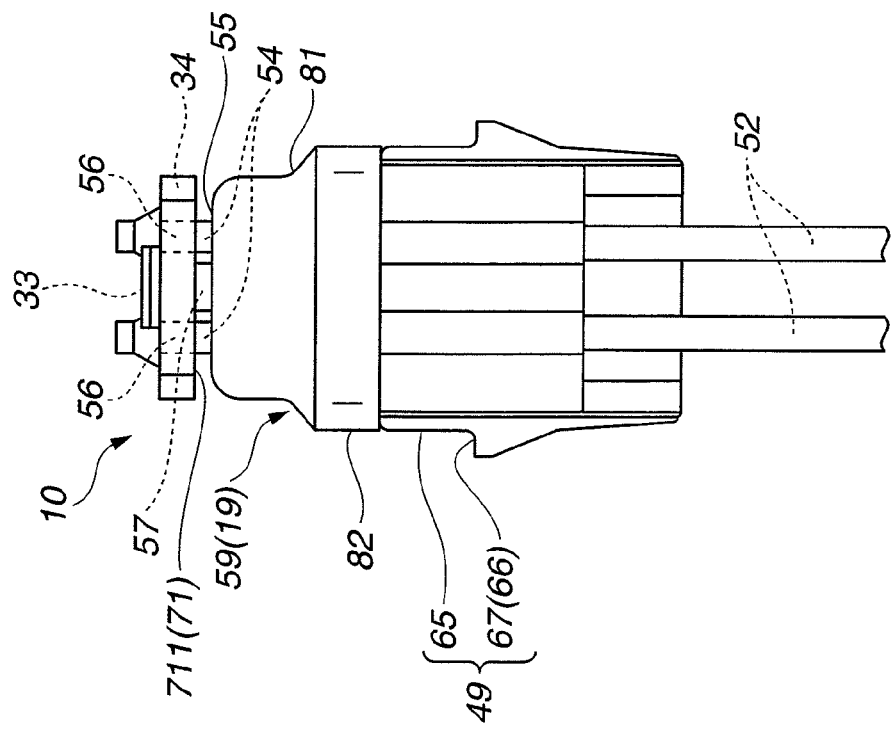

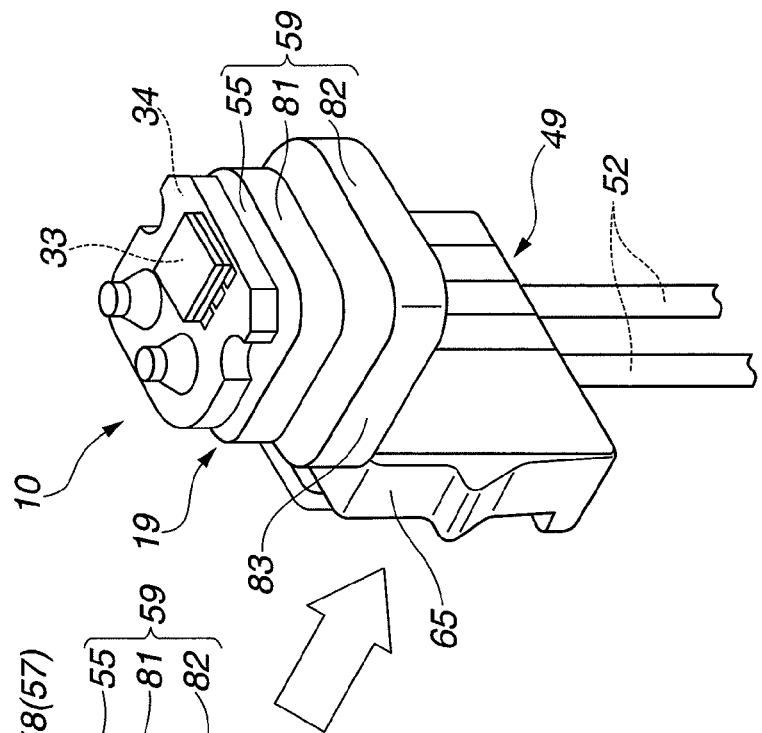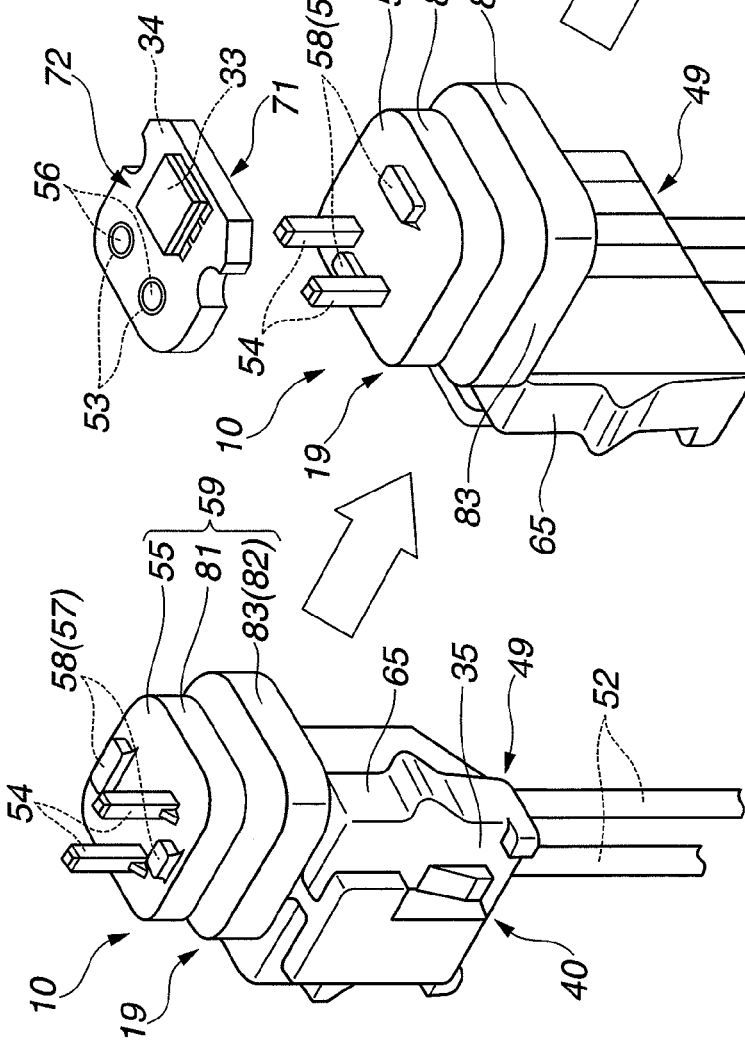

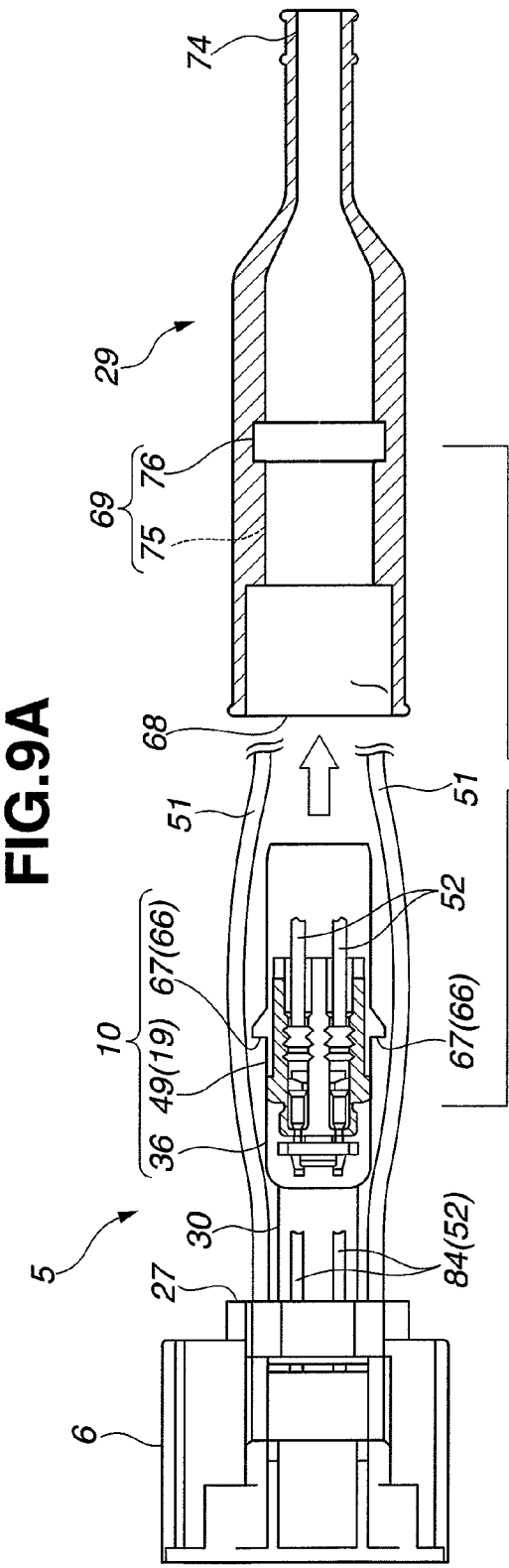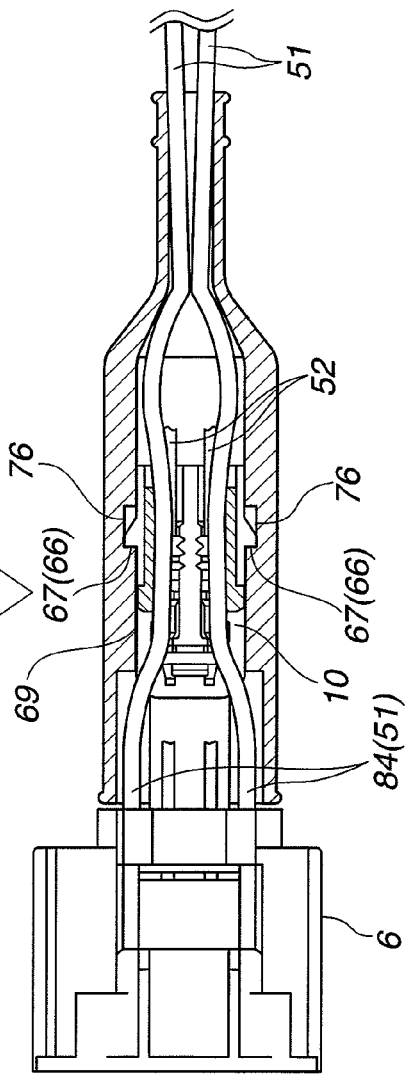

GAS SENSOR OUTPUT BASE SUPPORTING A CIRCUIT BOARD

BACKGROUND OF THE INVENTION

The present invention relates to a gas sensor for sensing the concentration of a gas component in a measurement gas to be examined.

A gas sensor of an earlier technology includes a sensing element producing a gas concentration signal representing the concentration of a gas component in a measurement gas (such as the NOx concentration of an exhaust gas of an internal combustion engine). The gas sensor is controlled by a sensor control device, which is configured to obtain the gas concentration signal from the sensing element by performing a sensor drive control of controlling a sensor main portion of the sensing element and a heater drive control of controlling a heater for heating the sensor main portion of the sensing element.

There may be subtle nonuniformity or dispersion from unit to unit in a gas concentration characteristic which is a characteristic representing a relationship between the concentration signal of the sensing element (the sensor main portion of the sensing element) and the concentration of a specified gas component, and a heater temperature characteristic which is a characteristic representing a relationship between the resistance (impedance) of the heater and the heater temperature.

Therefore, a gas sensor disclosed in a patent document JP 11-72478A (corresponding to U.S. Pat. No. 6,082,176) is provided with a storage medium for storing information (individual information) on the gas concentration characteristic and heater temperature characteristic of the corresponding gas sensor. The sensor control device obtains the stored individual information from the storage medium of the gas sensor and performs correction to reduce adverse influence of the dispersion.

Furthermore, a gas sensor disclosed in a patent document JP 2009-192486A includes a circuit board or wiring board equipped with a storage medium, a resin case including a mount surface supporting the circuit board, and a seal portion of a thermoplastic resin filled in the resin case to enclose the circuit board water-tightly.

SUMMARY OF THE INVENTION

During the process of forming the seal portion of the gas sensor of the earlier technology, by filling the thermoplastic resin at a high pressure in the resin case, the circuit board may be separated temporarily from the mount surface, and the thermoplastic resin may flow into a clearance formed between the circuit board and the mount surface. However, the separation is temporal and the clearance is irregular and unsteady, so that the thermoplastic resin could not be able to spread fully in the clearance within a limited amount of time. Thus, the spread of thermoplastic resin may be insufficient and nonuniform between the mount surface and circuit board, and there may be formed air bubbles or voids in the clearance. The air bubbles thus formed in the portion of the seal portion between the mount surface and circuit board tend to increase the possibility of cracks in the seal portion.

Therefore, it is an object of the present invention to provide a gas sensor having a seal structure adequate for preventing cracks.

According to one aspect of the invention, a gas sensor comprises: a sensing element to output a concentration signal representing a concentration of a gas component in a gas; a storage medium to store individual information prepared individually for the sensing element for use in control of the sensing element; a circuit board supporting the storage medium mounted on the circuit board; a seal portion of a resin covering the circuit board liquid-tightly; and an output base including a mount surface facing to the circuit board, and supporting a terminal portion which is connected with the circuit board and arranged to deliver the individual information through the circuit board. The output base includes a support projection projecting from the mount surface and including a support surface supporting the circuit board.

BRIEF DESCRIPTION OF THE DRAWINGS

FIG. 5 is a perspective view showing a bracket 30 and a holding portion 40 of the connection cable section 5 shown in FIGS. 3 and 4.

FIG. 6 (6A and 6B) is a view showing the structure of a circuit section 10 of the connection cable section 5 shown in FIGS. 3 and 4. FIG. 6 includes FIG. 6A showing the circuit section 10 in the sate in which a seal portion 36 is not yet formed, and FIG. 6B showing the circuit section 10 in the sate in which the seal portion 36 is formed.

FIG. 7 (7A, 7B and 7C) is a view for illustrating a process of attaching a circuit board 34 to an output base 19 of the connection cable section 5 shown in FIGS. 3 and 4

FIG. 9 (9A and 9B) is a view for illustrating a process of attaching the elastic member 29 to the connection cable section 5.

DETAILED DESCRIPTION OF THE INVENTION

Figure 1:
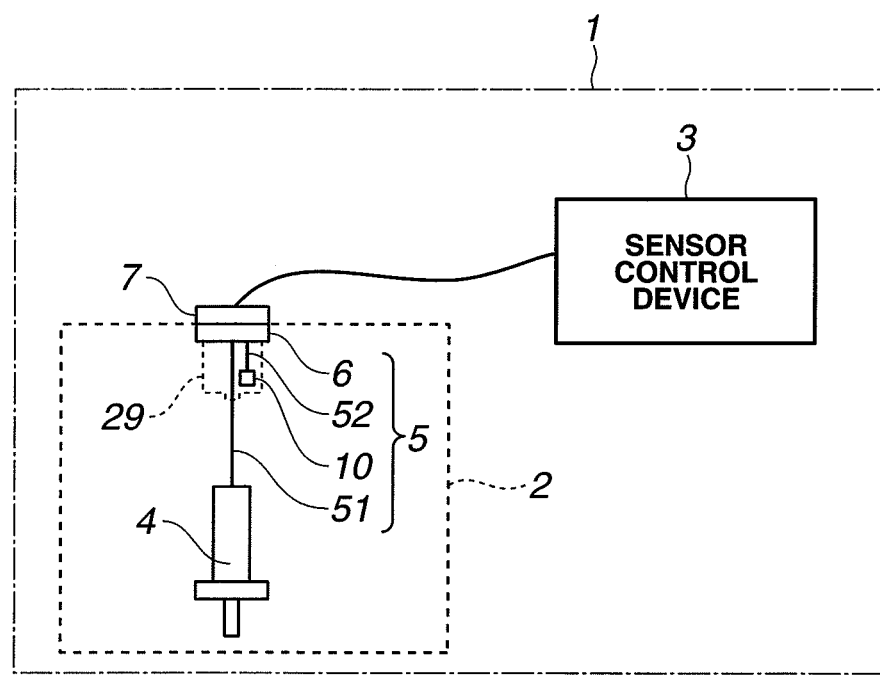
FIG. 1 is a schematic view showing gas sensing apparatus including a gas sensor (NOx sensor) 2 according to one embodiment of the present invention.
Figure 2:
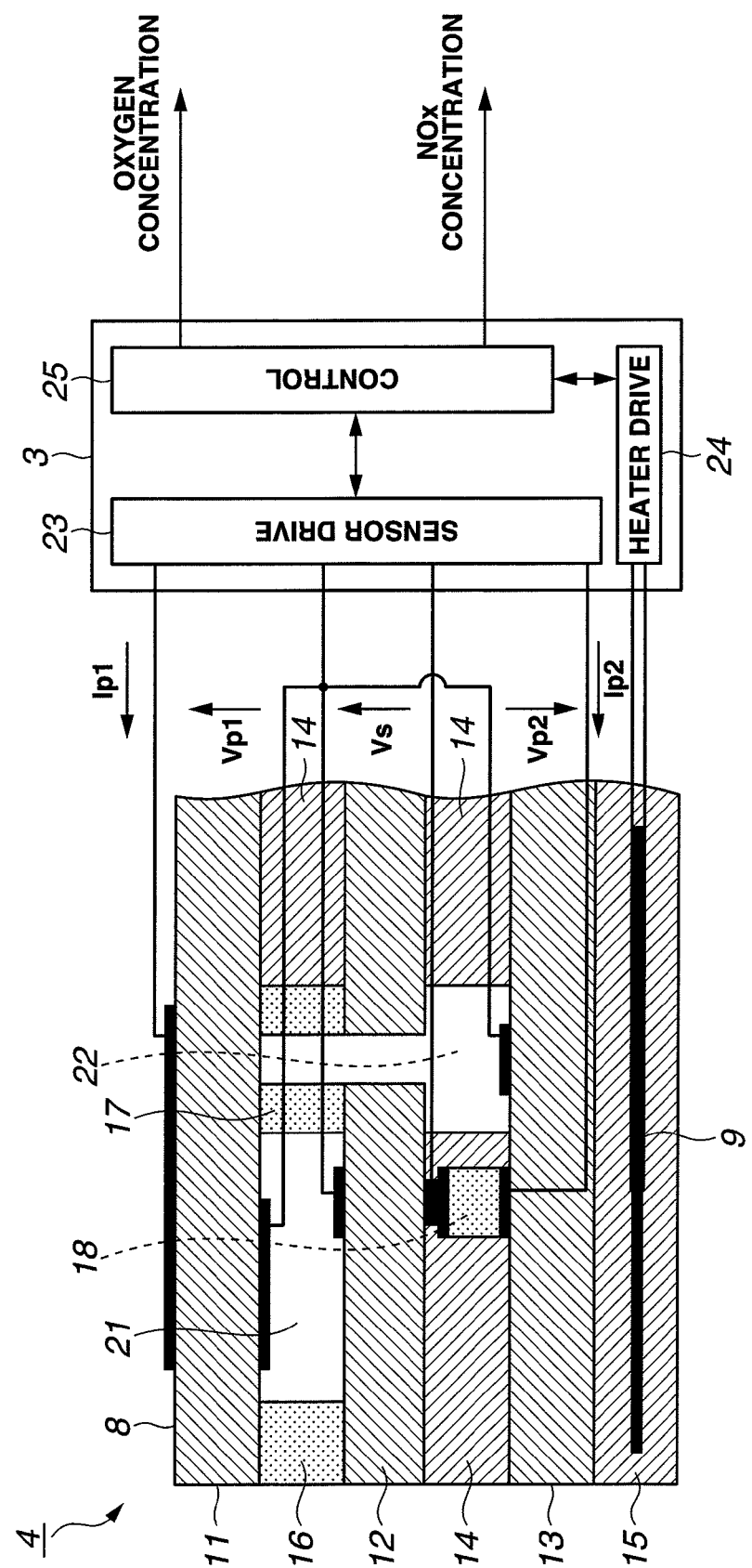
FIG. 2 is a view showing an internal structure of the gas sensing apparatus shown in FIG. 1.

<OVERALL STRUCTURE> FIG. 1 schematically shows the structure of a gas sensing apparatus or device 1 including a gas sensor 2 which, in this example, is an NOx sensor. FIG. 2 shows the internal structure of gas sensing apparatus 1.

As shown in FIG. 1, this gas sensing apparatus 1 includes the gas sensor 2 for sensing the concentration of a specified gas component (or specified gas) in a gas (or gas mixture) to be measured or examined, and a sensor control section or device 3 for controlling gas sensor 2. In this example, the gas to be measured is an exhaust gas (or exhaust gas mixture) of combustion apparatus such as an internal combustion engine of a vehicle or a boiler, the specified gas component is nitrogen oxide (NOx), and gas sensor 2 is the NOx sensor. NOx sensor 2 is adapted to be disposed in an exhaust passage of the combustion apparatus, and configured to sense the concentration of the nitrogen oxide as the specified gas component.

NOx sensor 2 includes a sensing element 4, a connection cable section 5 and an elastic member (connector boot) 29. The sensing element 4 is a sensing device to sense the NOx concentration, and to deliver a concentration signal corresponding to the NOx concentration, to the sensor control section 3. The connection cable section 5 includes a connector 6 connected, through a signal line (or first wiring section) including at least one first lead line 51, with the sensing element 4. The elastic member 29 of this example is a connection boot 29 attached to connection cable section 5.

The connector 6 is adapted to be connected with a connector 7 which is connected with sensor control section 3 in a detachable manner that connector 6 can be disconnected from connector 7. In the connected state in which connector 6 is fittingly engaged with connector 7, the connector 6 connects the NOx sensor 2 electrically with sensor control section 3. Thus, the gas sensing apparatus 1 is so arranged that NOx sensor 2 can be replaced easily by disconnecting the connectors 6 and 7 from each other.

The connection cable section 5 includes a circuit section 10 connected with connector 6 through an information line (or second wiring section) including at least one second lead line 52, and configured to perform operations of receiving and delivering data from and to the sensor control section 3 as mentioned later more in detail. The circuit section 10 is configured to store individual information preliminarily prepared for correcting the unit to unit nonuniformity of NOx sensor 2 (or sensing element 4), and to supply the individual information to sensor control section 3 in response to a request signal delivered from sensor control section 3 to request the individual information. In this example, the signal line (first wiring section) is a set of first lead lines 51 connecting the sensing element 4 with connector 6. The information line (or second wiring section) is a set of second lead lines 52 connecting the circuit section 10 with connector 6. A transmission line (or third wiring section) is a set of lead lines connecting the connector 7 with sensor control section 3. Each of the signal line, information line and transmission line is shown by a single line in FIG. 1, to facilitate understanding of the structure of gas sensing device 1.

As shown in FIG. 2, the sensing element 4 includes a main body 8 including a first oxygen pumping cell 11, an oxygen partial pressure sensing cell 12 and a second oxygen pumping cell 13 which are laminated through insulating layers 14. First oxygen pumping cell 11 includes a solid electrolyte layer of an oxygen ion conductive material such as zirconia, and porous electrodes (of a material such as platinum, platinum alloy, and/or a cermet including platinum and ceramic) formed on both sides of the solid electrolyte layer. Second oxygen pumping cell 13 includes a pair of electrodes formed on one side of a solid electrode layer.

Sensing element 4 further includes a heater 9 for heating the main body 8 with electricity from a battery (not shown). In the example of FIG. 2, heater 9 is formed in a sheet-like insulating layer 15 of an insulating material such as insulating ceramic (alumina, for example) united as an additional layer of the laminate of the main body 8. In this example, heater 9 is made of a material including Pt, as a main component.

The main body 8 includes a first measuring chamber 21 communicating through a first porous diffusion path 16 with a measurement gas space (inside the exhaust passage of the combustion apparatus), and a second measuring chamber 22 communicating with the first measuring chamber 21 through a second porous diffusion path 17. These measuring chambers are arranged to enable pumping operation of oxygen, respectively, by the first and second oxygen pumping cells 11 and 13. The oxygen partial pressure sensing cell 12 is arranged to measure the oxygen concentration difference between the first measuring chamber 21 and an oxygen reference chamber 18 in which the oxygen concentration is controlled at a constant level, and hence to measure the oxygen concentration in first measuring chamber 21.

The sensor control section or device 3 includes a sensor drive section 23 for driving the first oxygen pumping cell 11, oxygen partial pressure sensing cell 12 and second oxygen pumping cell 13, a heater driver section 24 for driving the heater 9, and a controlling section 25 for controlling the sensor drive section 23 and heater drive section 24. Heater driver section 24 of this example is arranged to turn on and off the supply of electricity to heater 9 and thereby to drive heater 9 in a PWM mode.

The controlling section 25 of sensor control section 3 performs a temperature control by heater 9 through heater drive section 24, and increases the temperature of the sensor main body 8 to an activation temperature (750° C., for example). In the thus-activated state, the controlling section 25 controls a first pump current Ip1 of first pumping cell 11, through sensor drive section 23, so as to hold a voltage Vs between both ends of oxygen partial pressure sensing cell 12 at a predetermined constant voltage (425 mV, for example). By this control of first pump current Ip1, the oxygen concentration in first measuring chamber 21 is held, through first oxygen pumping cell 11, at a predetermined low concentration or minimum setting ($\approx$0%). Thus, the first pumping current Ip1 is controlled to a value corresponding to the oxygen concentration in the measurement gas.

At the same time, through sensor drive section 23, the controlling section 25 impresses the second oxygen pumping cell 13 with a constant second pump voltage Vp2 (450 mV, for example) in the direction drawing out the oxygen from second measuring chamber 22. When the oxygen concentration in first measuring chamber 21 is held at the predetermined low concentration and the second pump voltage Vp2 is held at the predetermined constant voltage in this way, then the porous electrode of second oxygen pumping cell 13 acts as a catalyst, in the second measuring chamber, for decomposing NOx in the measurement gas (namely, the gas flowing in from first measuring chamber 21, and having the oxygen concentration controlled at the predetermined low level) into nitrogen and oxygen, and the oxygen formed by the decomposition is pumped out from second measuring chamber 22 toward the other electrode of second pumping cell 13 facing the oxygen reference chamber 18. A second pump current Ip2 flowing during this has a value corresponding to the NOx concentration of the measurement gas.

The controlling section 25 of gas control section 3 performs a gas concentration sensing process of sensing the oxygen concentration and NOx concentration of the exhaust gas in accordance with the concentration signal (first pump current Ip1 and second pump current Ip2) outputted from sensor main portion 8, and supplies the concentration information (on the oxygen concentration and the NOx concentration) to an external device or system (such as an engine ECU).

The controlling section 25 of gas control section 3 performs an information acquisition process of outputting the information request signal to the circuit section 10 of NOx sensor 2 and obtaining the individual information from circuit section 10, and sets a characteristic representing a relationship between the first pump current Ip1 and the oxygen concentration, and a characteristic representing a relationship between the second pump current Ip2 and the NOx concentration. The controlling section 25 of gas control section 3 is configured to perform an output correction for the sensor main portion 8 in accordance with the individual information obtained by the information acquisition process at the time of performing the gas concentration sensing process.

Figure 3:
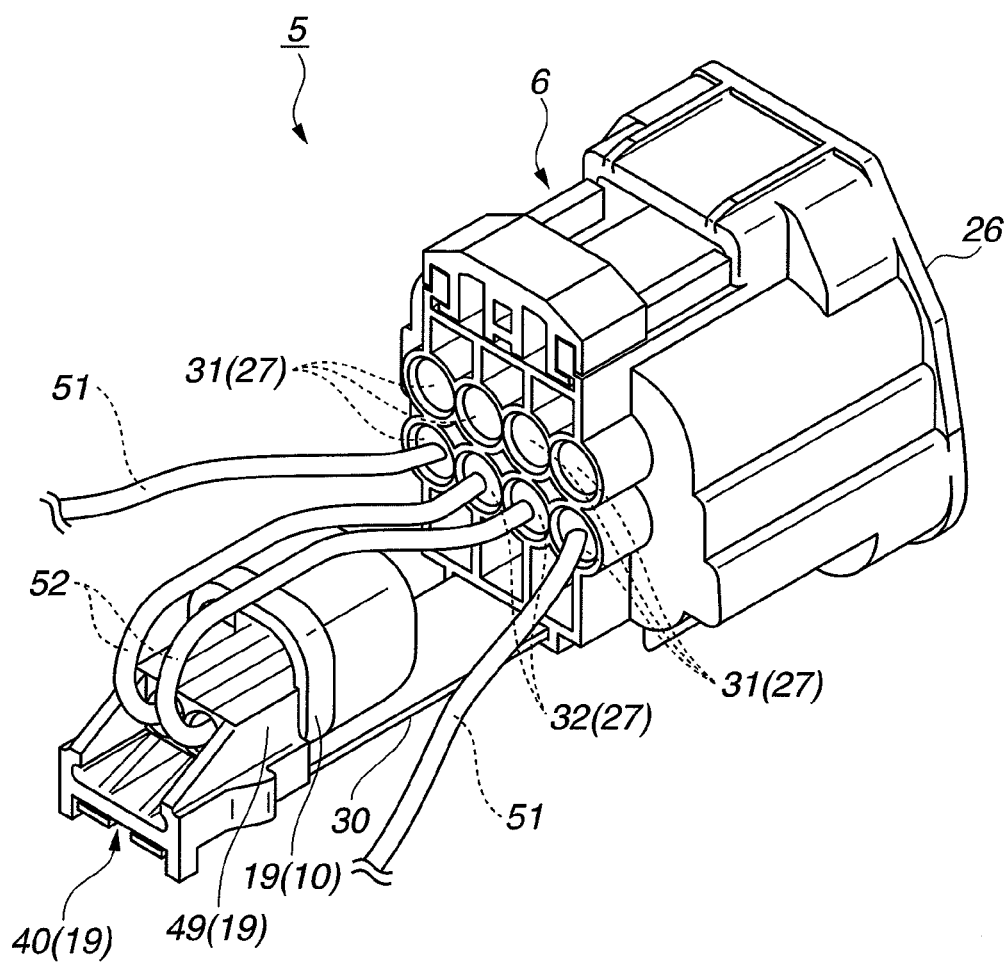
FIG. 3 is a perspective view showing a connection cable section 5 of the gas sensor 2 shown in FIG. 1
Figure 4:
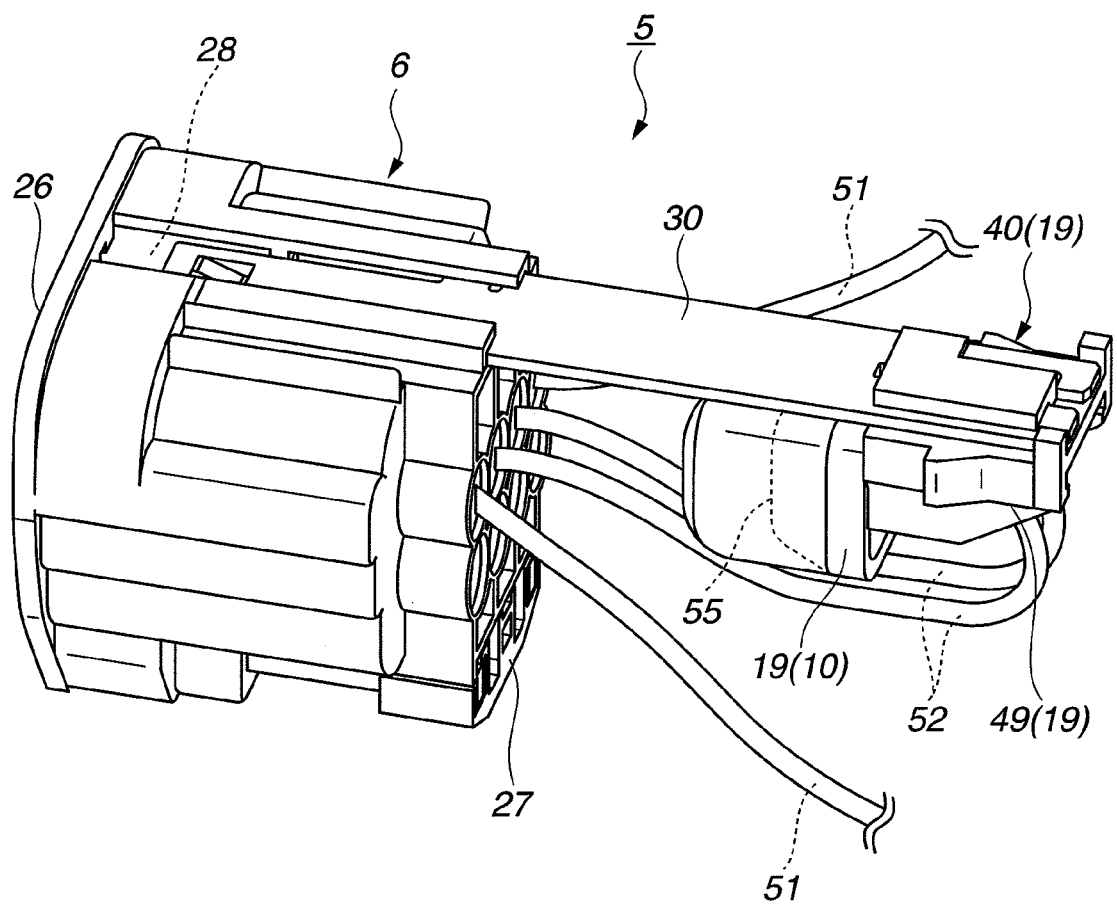
FIG. 4 is a perspective view showing the connection cable section 5 as viewed from a different direction.

<CONNECTION CABLE SECTION> FIGS. 3 and 4 show, in perspective, the structure of connection cable section 5. FIG. 3 is a perspective view as viewed obliquely from above. FIG. 4 is a perspective view as viewed obliquely from below. Although FIGS. 3 and 4 (and FIG. 9) show only two first lead lines 51, there are provided, in practice, three or more first lead lines 51 connected with connector 6. (In this example, there are six lead lines 51.)

As shown in FIGS. 3 and 4, the connection cable section 5 includes an output base 19 and a bracket 30 in addition to the above-mentioned connector 6 and circuit section 10. Output base 19 forms circuit section 10. Bracket 30 is a long plate-shaped (metallic) member for connecting output base 19 and connector 6. As mentioned later more in detail, the output base 19 includes a box-shaped case portion 49 enclosing part of at least one second lead line 52.

Connector 6 includes a fitting face 26 adapted to be connected fittingly with connector 7 connected with sensor control section 3, an inserting face 27 having at least one first insertion hole 31 to which one first lead line 51 is inserted, at least one second insertion hole 32 to which one second lead line 52 is inserted, and a bracket attachment face 28 to which bracket 30 is attached.

Each lead line 52 projecting from case portion 49 of output base 19 is bent backward in a direction opposite to a direction of lead line 52 inside the case portion 49, and inserted into a corresponding one of second insertion holes 32 of the insertion face 27 of connector 6, so that the lead line 52 is electrically connected with connector 6. Second lead lines 52 as well as the circuit section 10 including output base 19 are inserted into connector boot 29 (cf. FIG. 8 and FIG. 9) for protecting the connection part between lead lines 51 and 52 and connector 6. In this example, each of the second lead line 52 includes a first segment extending in the case portion 49 in a direction away from the connector 6, a second segment bent in the form of the letter U, and a third segment extending to the connector 6 over the output base 19.

Output base 19 is formed with a bracket attachment surface 35 (cf. FIG. 5) which is located on a lower side of the case portion 49, which is approximately rectangular and which is adapted to abut on bracket 30 attached to attachment surface 35. Output base 19 includes a holding or holder portion 40 for holding bracket 30. This holding portion 40 is arranged to hold the bracket 30 so as to clamp bracket 30 between bracket attachment face 35 and holding portion 40 (cf. FIG. 5 and FIG. 4).

<BRACKET AND HOLDING PORTION> FIG. 5 shows in perspective the bracket 30 and the holding portion 40 of output base 19. Bracket 30 extends longitudinally from a first end 41 to a second end 42. As shown in FIG. 5, bracket 30 includes a slider portion 50 and a hook portion 60 in a first end portion near first end 41. Slider portion 50 includes a pair of confronting inside slider surfaces 37 formed by a cutout extending from first end 41 of bracket 30 toward the second end 42. This cutout is formed between a first leg which is formed with the hook portion 60 and one of the inside slider surfaces 37, and a second leg which is formed with the other of the inside slider surfaces 37 and which extends longitudinally side by side with the first leg to the first bracket end 41. Hook portion 60 includes a stopper surface 38 formed by forming a recess in one of the slider surfaces 37. This stopper surface 38 faces toward second end 42. Bracket 30 of this example is in the form of a long flat (metallic) plate. In a second end portion near second end 42, bracket 30 includes an attachment hole 39 for fastening the bracket 30 to connector 6. The first end 41 and second end 42 of bracket 30 can be referred to as front bracket end and rear bracket end, respectively. The rear bracket end 42, connector 6 and the connection therebetween are substantially identical to those disclosed in a patent document JP 2009-121975A. Accordingly, explanation is omitted, and the explanation in this Japanese patent document is hereby incorporated by reference.

Holding portion 40 of output base 19 includes a stopper portion 45, a guide wall 46, a limiting plate portion 47, and side wall portions 44. Stopper portion 45 is a projection which projects from bracket attachment surface 35 and which is adapted to be hooked by hook portion 60 of bracket 30. Guide wall 46 projects and stands from bracket attachment surface 35, has a shape allowing sliding movement of inside slider surfaces 37 of slider portion 50 of bracket 30, and includes an outside wall surface 48 for guiding the hook portion 60 to stopper portion 45. Guide wall 46 is adapted to be inserted into the cutout defined between the inside slider edge surfaces 37 of bracket 30. Limiting plate portion 47 is arranged to limit movement of the slider portion 50 of bracket 30 in a direction perpendicular to bracket attachment surface 35. In this example, the bracket attachment surface 35 is substantially flat. In the state in which bracket 30 is inserted into holding portion 40, the front portion of bracket 30 is confined between the bracket attachment surface 35 and the limiting plate portion 47. Two of side wall portions 44 are arranged to clamp or hold a part of the front bracket end 41 firmly therebetween.

As shown by a (single-head) arrow in FIG. 5, a first direction is a guide direction in which hook portion 60 of bracket 30 is guided along the outside wall surface 48 of guide wall 46 to stopper portion 45. A second direction (shown by a double-head arrow) is an attachment surface direction perpendicular to the bracket attachment surface 35 which is a substantially flat surface in this example. A third direction (shown by a double-head arrow) is an outside wall surface direction perpendicular to (substantially flat) outside wall surface 48 of guide wall 46.

Guide wall 46 extends, in the guide direction, from a first wall end to a second wall end, and the length of guide wall portion 46 from the first wall end to the second wall end is approximately equal to the length of the inside wall surface 37 of slider portion 50 of bracket 30. The bracket attachment surface 35 is substantially rectangular flat surface extending in the guide direction from a first (shorter) side to a second (shorter) side opposite to the first (shorter) side. The first wall end of guide wall 46 is located approximately at the middle of the first (shorter) side of the substantially rectangular bracket attachment surface 3. From the first wall end, the guide wall 46 extends in the guide direction toward the middle of the second (shorter) side of bracket attachment surface 35, and terminates at the second wall end without reaching the second (shorter) side of bracket attachment surface 35. Thus, the second wall end of guide wall portion 46 is close to, but slightly away from the middle of the second side of the substantially rectangular bracket attachment surface 35. The side wall portions 44 are formed at both ends of the second (shorter) side of bracket attachment surface 35. Guide wall 46 and side wall portions 44 are so located that they are not overlapped as viewed in the outside wall surface direction.

Stopper portion 45 is located at a position which does not overlap the limiting plate portion 47 as viewed from the attachment surface direction, and which adjoins the outside wall surface 48 of guide wall portion 46. Moreover, stopper portion 45 includes an abutment surface (not shown in FIG. 5) which abuts on the stopper surface 38 of bracket 30 in the engaged state engaged with hook portion 60. This abutment surface of stopper portion 45 is substantially flat and flush with the second end surface of guide wall 46 so that a substantially flat end surface is formed continuously over these surfaces with no step. This flat end surface faces in the guide direction. The stopper surface 38 of bracket 30 faces in the opposite direction opposite to the guide direction in the engaged state of the bracket 30 and the holder portion 40 shown in FIG. 4.

Limiting plate portion 47 includes a shorter side portion 61 and a longer side portion 62. The shorter side portion 62 extends over a first half region of the bracket attachment surface 35, and the longer side portion 62 extends over a second half region of the bracket attachment surface 35. The substantially rectangular bracket attachment surface 35 is divided into the first and second half regions by the guide wall 46. Stopper portion 45 is formed in the first half region, and the second half region is the region in which no stopper portion 45 is formed. The longer side portion 62 includes an inside surface which confronts (the second half region of) bracket attachment surface 35, and which is substantially parallel to the substantially flat bracket attachment surface 35.

The shorter side portion 61 includes an inside slant surface 63 which confronts (the first half region of) bracket attachment surface 35, and which is inclined so that the distance from (the first half region of) the bracket attachment surface 35 becomes gradually greater in the guide direction. This inside slant surface 63 is formed entirely over the inside surface of shorter side portion 61 confronting bracket attachment surface 35. The stopper portion 45 includes an outside slant surface 64 whose height from bracket attachment surface 35 becomes greater gradually in the guide direction.

In the illustrated example, the stopper portion 45, guide wall portion 46 and limiting plate portion 47 are formed on a first side of an imaginary flat plane, whereas the side wall portions 44 are formed on a second side of the imaginary flat plane which is perpendicular to the bracket attachment surface 35, which extends substantially in parallel to the shorter sides of the substantially rectangular flat bracket attachment surface 35 between the shorter sides, which divides the substantially rectangular flat bracket attachment surface 35 into a broad rectangular region extending from the first shorter side to the imaginary flat plane and a narrow rectangular region extending from the second shorter side to the imaginary flat plane. The stopper portion 45, guide wall portion 46 and limiting plate portion 47 are formed only in the broad rectangular region, whereas the side wall portions 44 are formed only in the narrow rectangular region. The shorter side portion 61 of limiting plate portion 47 extends in the guide direction and terminates without reaching the position of stopper portion 46 so that the stopper portion 46 is not covered by shorter side portion 61 of limiting plate portion 47.

The bracket 30 is inserted into the thus-constructed holding portion 40 of output base 19 in the guide direction so that the slider portion 50 slides along guide wall 46, and the guide wall 46 is inserted into the cutout defined by inside slider surfaces 37. During this sliding movement, the first leg of (metallic) bracket 30 having hook portion 60 is slightly deformed elastically by the outward slant surface 64 of stopper portion 45 and the inside slant surface 63 of limiting plate portion 47, and the hook portion 60 is engaged with stopper portion 45 so that stopper surface 38 of hook portion 60 abuts against the end surface of stopper portion 45.

In the engaged state of the thus-constructed bracket 30 and holding portion 40, the stopper portion 45 limits movement or extraction of bracket 30 in an extracting direction opposite to the guide direction by abutting against the stopper surface 38 of hook portion 60 of bracket 30, and the first wall end of guide wall 46 facing in the extracting direction limits movement of bracket 30 in the guide direction. Furthermore, the limiting plate portion 47 limits movement of bracket 30 in the attachment surface direction by putting the first leg of bracket 30 between shorter side portion 61 and the first half region of bracket attachment surface 35, and putting the second leg of bracket 30 between longer side portion 62 and the second half region of bracket attachment surface 35. Movement of bracket 30 in the outside wall surface direction is limited by guide wall 46 put between slider surfaces 37 of slider portion 50, and the side wall portions 44 holding the first bracket end 41 therebetween.

<CIRCUIT SECTION> FIG. 6 (6A and 6B) illustrates the structure of circuit section 10 of connection cable section 5. FIG. 6A shows the state before the formation of seal portion 36 and FIG. 6B shows the state after the formation of seal portion 36. FIG. 7 (7A, 7B and 7C) illustrates a process of attaching a circuit board 34 to output base 19.

As shown in FIG. 6, the circuit section 10 includes a storage medium 33, the circuit board 34 including a connection portion 53 (cf. FIG. 7), the output base 19 having a mount surface 55 and a seal portion 36. The storage medium (or storage device) 33 is a device for storing individual information or data on the NOx sensor 2 to which this circuit section 10 is attached. Storage medium 33 is mounted on the circuit board 34. Circuit board 34 (or interconnection or wiring board) is a plate-shaped member including at least one connection portion 53 (cf. FIG. 7) which is connected electrically with storage medium 33 (through conductive wiring). The output base 19 has the mount surface 55 receiving at least one columnar terminal portion 54 extending through the mount surface 55. Columnar terminal portion 54 is configured to transmit the individual information from storage medium 33 through connection portion 53. Seal portion 36 is a cover member covering the circuit board 34 watertightly or liquidtightly. The mount surface 55 of output base 19 faces toward the insertion face 27 of connector 6 in the assembled state in which output base 19 is connected with connector 6 by bracket 30 (cf. FIG. 4).

The individual information memorized in storage medium 33 of this example includes sensor characteristic information used for output correction or modification of the sensing element. The sensor characteristic information may include information (O2 gain and O2 offset) for setting the relationship representing the characteristic between the first pump current Ip1 and the oxygen concentration, and information (NOx gain and NOx offset) for setting the relationship representing the characteristic between the second pump current Ip2 and the NOx concentration. Sensing elements 4 produced by production process of NOx sensors 2 are inspected individually with a predetermined testing apparatus. The individual information is information obtained during this test or inspection process for inspecting sensing elements 4 individually or one by one. Thus, each of the sensing elements 4 is inspected to obtain individual information unique to that sensing element 4, and this individual information is stored in one of the storage media 33. Each sensing element 4 is thus paired with a unique one of the storage media 33 storing the individual information unique to that sensing element 4, and incorporated in one of the NOx sensors 2 together with the corresponding storage medium 33. The output correction or modification of the sensing element is explained in the before-mentioned patent document JP 11-72478 corresponding to U.S. Pat. No. 6,082,176. Accordingly, further explanation is omitted, and the explanation in this JP or US patent document is herein incorporated by reference.

Output base 19 is made of a resin such as a nylon resin (PA66 nylon, for example). As shown in FIG. 7, output base 19 includes a base portion 59 in addition to the before-mentioned case portion 49 and holding portion 40. The base portion 59 includes at least one projecting portion or support projection 57 projecting from mount surface 55. Base portion 59 has an inside cavity (not shown) communicating with the inside of case portion 49. In this cavity, terminal portion 54 is connected with second lead line 52. Base portion 59 is formed at such a position that base portion 59 does not interfere with bracket 30 when bracket 30 is attached to bracket attachment surface 35 (cf. FIG. 5 and FIG. 7).

Base portion 59 includes a first circumferential side surface 81 and a second circumferential side surface 82 in addition to mount surface 55. First circumferential side surface 81 extends from the rim of mount surface 55. Second circumferential side surface 82 extends from case portion 49. Second circumferential side surface 82 extends outwards beyond the first circumferential side surface 81. Accordingly, there is formed a shoulder surface or step surface between the first and second circumferential side surfaces 81 and 82. Second circumferential side surface 82 includes a region 83 which is substantially parallel to side surface 65 of case portion 49. This region 83 is referred to as object surface 83. This object surface 83 is formed at such a position that object surface 83 does not project outwards beyond side surface 65 of case portion 49. In the example shown in FIG. 7, object surface 83 is flush with side surface 65 so that there is formed no step therebetween. Case portion 49 includes first and second side surfaces 65, and the base portion 59 is formed between first and second side surfaces 65 without projecting outwards beyond the width between first and second side surfaces 65.

The support projection 57 has a support surface 58 (top surface) supporting circuit board 34. Circuit board 34 has first and second board surfaces 71 and 72 which are opposite to each other. The first board surface 71 of circuit board 34 faces toward mount surface 55 whereas second board surface 72 faces in the opposite direction away from mount surface 55, in the state in which circuit board 34 is supported by support projection 57. Storage medium 33 is mounted on second board surface 72. Thus, circuit board 34 is located between the storage medium 33 mounted on second board surface 72 and the support projection 57 supporting the first board surface 71 so that the sizes of circuit board 34 and output base 19 (base portion 59) can be reduced.

There are provided two of the support projections 57 in this example. The two support projections 57 are formed, respectively, in two regions into which the mount surface 55 is divided. Circuit board 34 of this example includes at least one through hole 56 extending through circuit board 34 in the thickness direction of circuit board 34 from first board surface 71 to second board surface 72. Terminal portion 54 is inserted through the through hole 56, and thereby circuit board 34 is supported on the support surfaces 58 of support projections 57. Thus, base portion 59 is constructed to limit movement of circuit board 34 in the direction normal to the board surfaces 71 and 72 with support projections 57, and to limit movement of circuit board 34 in directions parallel to the board surfaces 71 and 72 with the terminal portion 54 inserted in the through hole 56.

Connection portion 53 of this example is formed around the through hole 56 in the second board surface 72. Connection portion 53 is joined with terminal portion 54 (by soldering, for example) in the state in which the connection portion 53 is electrically connected with storage medium 33 mounted on circuit board 34 and the circuit board 34 is supported on the support surface(s) 58 of support projection(s) 57. In this example, there are provided a plurality of terminal portions 54, a plurality of through holes 56 and a plurality of connection portions 53, and each terminal portion 54 is inserted in a unique one of the through holes 56 and electrically connected with storage medium 33 through the connection portion 53 formed around that through hole 56.

In this way, as shown in FIG. 6, circuit board 34 is supported by one or more support projections 57 (with the top surfaces 58 of projections 57) so that there is formed a clearance between mount surface 55 of output base 19 and the first board surface 71 of circuit board 34 (to be exact, a plain region 711 of first board surface 71 excluding the regions supported by support projections 57 and the regions of through holes 56 through which terminal portions 54 pass, respectively). The thickness or height of this clearance is determined by the height of support projection(s) 57.

Circuit board 34 is configured to receive the information request signal to request the individual information from the controlling section 25 of sensor control device 3 through at least one connection portion 53 and terminal portion 54 which are connected together, and to supply the individual information stored in storage medium 33, to the controlling section 25 of sensor control device 3, in response to the information request signal.

As shown in FIG. 6, the seal portion 36 is formed by filling the thermoplastic resin around the circuit board 34 and the first circumferential side surface 81 of output base 19 in the state in which the terminal portion 54 is connected with the connection portion 53 (at each through hole 56). The thermoplastic resin used as the material of seal portion 36 is a resin having a higher thermal expansion coefficient (or coefficient of thermal expansion) higher than the thermal expansion coefficient of the resin of output base 19 (base portion) which is the nylon resin in this example. In this example, the thermoplastic resin is a hot-melt resin having a higher thermal expansion coefficient (Macromelt (registered trademark) of Henkel Japan Ltd.). In this embodiment, there is formed, between the mount surface 55 of output base 19 and the first board surface 71 (the plain region 711), the clearance determined by the height of support projection(s) 57. Therefore, in the filling process, the thermoplastic resin can flow smoothly and entirely into the clearance and enclose the circuit board 34 securely in the watertight manner.

Figure 11:
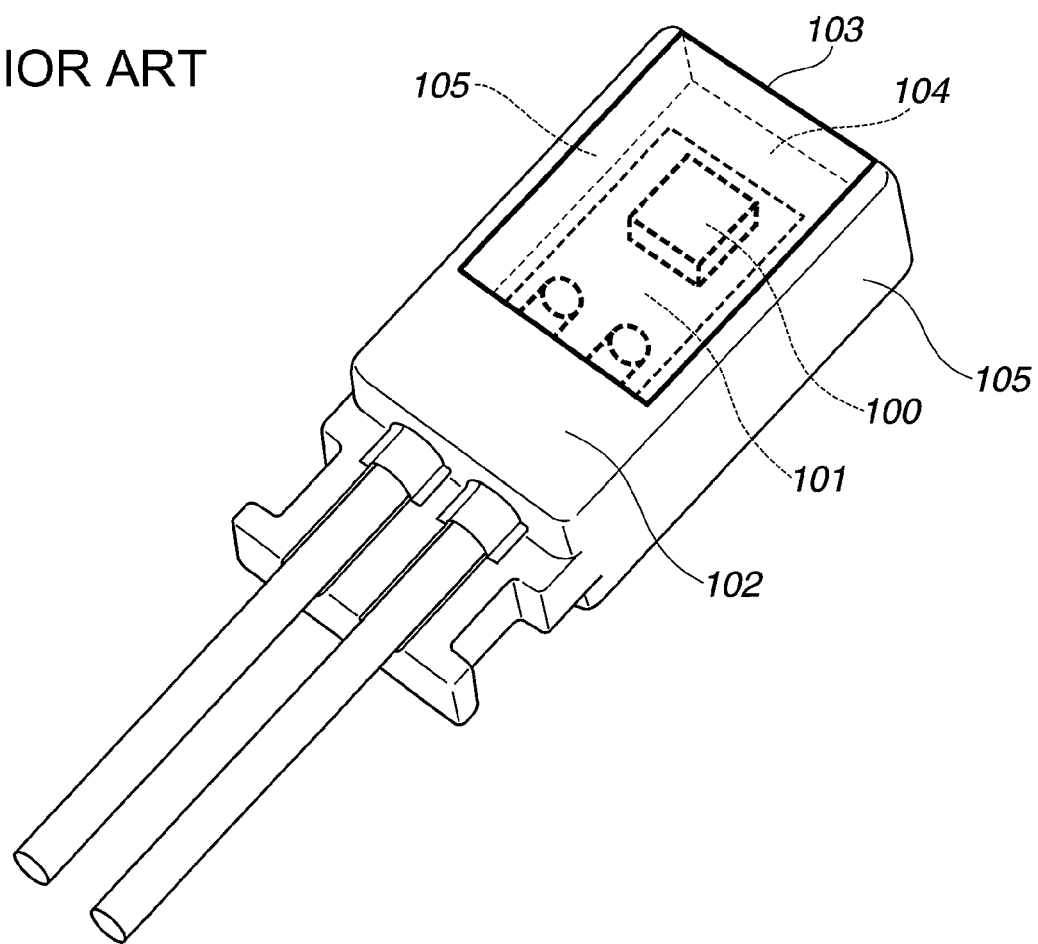
FIG. 11 is a perspective view showing a seal structure in a resin case 102 of a gas sensor of earlier technology.

In the case of a gas sensor of earlier technology having a circuit or wiring board 101 supporting a storage medium 100 and a resin case 102 encasing the circuit board 101 as shown in FIG. 11, a seal portion 103 for sealing circuit board 101 liquid-tightly is formed by filling a thermoplastic resin in the resin case 102 at a position bounded by side walls 105. Therefore, when the thermal expansion coefficient of the thermoplastic resin is higher than that of the resin (nylon resin) of resin case 102, the seal portion 103 might exfoliate from the resin case 102 because of changes of the surrounding temperature, and might become unable to maintain the water proofing function.

Specifically, the seal portion 103 is formed in the closed space confined by the side walls 105 of resin case 102. Therefore, when seal portion 103 is expanded by a temperature increase, the resin case 102 is forced to expand to the same degree. In the case of a temperature decrease, on the other hand, the seal portion 103 contracts to a greater degree than the resin case 102. In this way, the seal portion 103 might be removed from side walls 105 of resin case 102 as a result of repetition of such expansion and contraction.

In the case of the gas sensor 2 according to the embodiment of the present invention, by contrast, the seal portion 36 is formed, as shown in FIG. 6, so as to cover the first circumferential side surface 81 of base portion 59. Therefore, seal portion 36 can expand outwards without being limited, with increase of the surrounding temperature even if the thermal expansion coefficient of the thermoplastic resin (of seal portion 36) is higher than that of the resin (nylon resin) of base portion 59. During the outward expansion of seal portion 36, the base portion 59 is not forced to expand together. Therefore, the seal structure of this embodiment can prevent or restrain exfoliation of seal portion 36 from base portion 59 even if expansion and contraction are repeated in seal portion 36 and base portion 59.

The case portion 49 includes at least one stopper projection 66 (or lateral projection) projecting from one of side surfaces 65 of case portion 49. Stopper projection 66 includes a stopper surface 67 which is perpendicular to the side surface 65 in this example. Stopper surface 67 faces in a direction opposite to an inserting direction of insertion of output base 19 into the connector boot 29. In this example, the stopper projection (lateral projection) 66 is formed in each of the first and second side surfaces 65.

Figure 8:
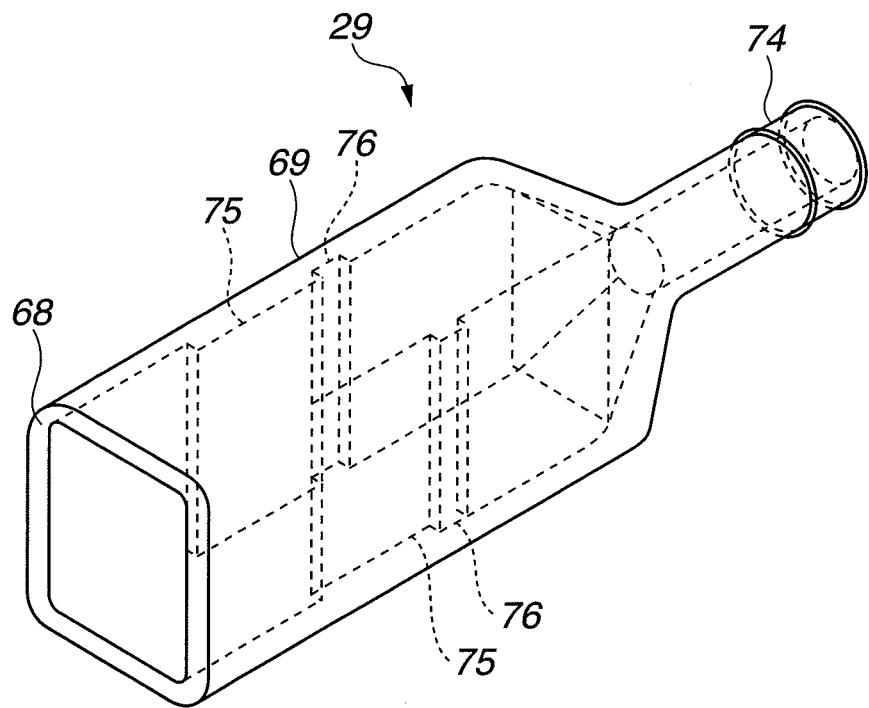
FIG. 8 is a perspective view showing an elastic member (connector boot) 29 used in the connection cable section 5 shown in FIGS. 3 and 4

<ELASTIC MEMBER (CONNECTOR BOOT)> FIG. 8 shows, in perspective, the elastic member 29 which is connector boot 29, in this example. FIG. 9 (9A and 9B) illustrates a process of attaching connector boot 29 to connection cable portion 5. FIG. 9 includes FIGS. 9A and 9B showing connection cable portion 5 as viewed from a position above connector 6, and showing the connector boot 29 and circuit section 10 in section.

As shown in FIGS. 8 and 9, connector boot 29 is a tubular elastic member of a rubber. Connector boot 29 includes an open end portion 68 (or larger end portion) and a receiving portion 69 (or intermediate portion) adjacent to the open end portion 68. The open end portion 68 is adapted to enclose connector's side end portions 84 of lead lines 51 and 52 in the state in which the output base 19 formed with seal portion 36 is connected with connector 6 by bracket 30. The receiving portion 69 is adapted to receive the circuit section 10 (circuit section 10 and second lead lines 52). In this example, the receiving portion 69 is adapted to further receive part of the first lead lines 51 connected with connector 6.

Connector boot 29 further includes at least one groove 76 formed in an inside wall surface 75 of receiving portion 69. Groove 72 is adapted to receive the stopper (lateral) projection 66 of output base 19 (case portion 49) in the state in which the connector's side end portions 84 of lead lines 51 and 52 are enclosed in open end portion 68. Groove 76 includes a side surface abutting on the stopper surface 67 of stopper (lateral) projection 66, as shown in FIG. 9B. As shown in FIG. 8, connector boot 29 of this example includes two of the grooves 76 adapted to engage, respectively, with the two stopper lateral projections 66.

Connector boot 29 further includes a takeout portion 74 (or smaller end portion) having an opening for drawing out the first lead lines 51 from the receiving portion 69. The first lead lines 51 projecting from takeout portion 74 are covered with a coating (or covering) member (not shown) fitting over the takeout portion 74.

Thus, connector boot 29 protects the circuit section 10 and lead lines 51 and 52 against dust and dirt with receiving portion 69 enclosing the circuit section 10 and lead lines 51 and 52, and protects the lead lines 51 and 52 at or neat the insertion face 27 of connector 6, against undesired bending with the open end portion 68 enclosing the connector's side end portions 84 of lead lines 51 and 52.

<Effects> As explained above, the gas (NOx) sensor 2 according to this embodiment is arranged to support the circuit board 34 with at least one support projection 59 (support surface 58) of output base 19 in the state in which there is formed a clearance or interspace between the mount surface 55 of output base 19 and the circuit board 34 (first board surface 71). Therefore, in the process of forming the seal portion 36 by filling the resin (thermoplastic resin) so as to enclose the circuit board 34, the resin can readily spread entirely over the clearance or interspace between circuit board 34 and mount surface 55.

Therefore, the structure of the gas sensor 2 according to the embodiment can prevent formation of voids (air bubbles) in the region between circuit board 34 and mount surface 55, and hence prevent cracks from being formed in the seal portion 36 by temperature changes.

Moreover, the thermoplastic resin can flow smoothly into the clearance between the circuit board and the mount surface of the output base. Therefore, the structure of the gas sensor 2 according to the embodiment can facilitate the filing process and reduce the required time of the filling process, so that the production efficiency is improved.

In the case of the output base 19 formed with two or more support projections 57, the output base can support the circuit board 34 firmly to maintain the clearance between the circuit board and the mount surface steadily and securely during the filling process, and thereby makes it possible to form the seal portion 36 into an optimum shape. In the case of the arrangement in which storage medium 33 is mounted on the second board surface 72 opposite to the first board surface 71 facing to mount surface 55, it is possible to reduce the areas of first and second board surfaces 71 and 72 because the region supporting storage medium 33 and the region abutting on the support surface of the support projection 57 are separated, instead of both regions being formed in the same board surface. In this case, therefore, it is possible to reduce the sizes of the circuit board and output base. In the illustrated example, circuit board 34 is formed with at least one through hole 56, the connection portion 53 is formed around the brim of through hole 56 in or on at least one of the first and second board surfaces 71 and 72, and the through hole 56 has an inside size or an inside diameter allowing the insertion of the terminal portion 54 therethrough. The terminal portion 54 inserted into the through hole 56 can determine the position of circuit board 34 and hold the circuit board 34 firmly at the position during the filling process, to form the seal portion 36 optimally. The connection portion 53 provided around the through hole 56 is effective for facilitating the operation of joining the terminal portion to the connection portion.

Moreover, elastic member 29 can be attached to output base 19 simply by inserting output base 19 into tubular elastic member, and engaging the stopper lateral projection(s) 66 of output base 19 in the groove(s) 76 of elastic member 29, without the need for fastening the elastic member to output base 19 with an adhesive, to the advantage of cost reduction. Furthermore, elastic member 29 can be removed from output base 19 by the use of the elasticity of elastic member 29, to the advantage of maintenance in case of abnormality in the connection between lead lines 51 or 52 with connector 6.

Figure 10A:
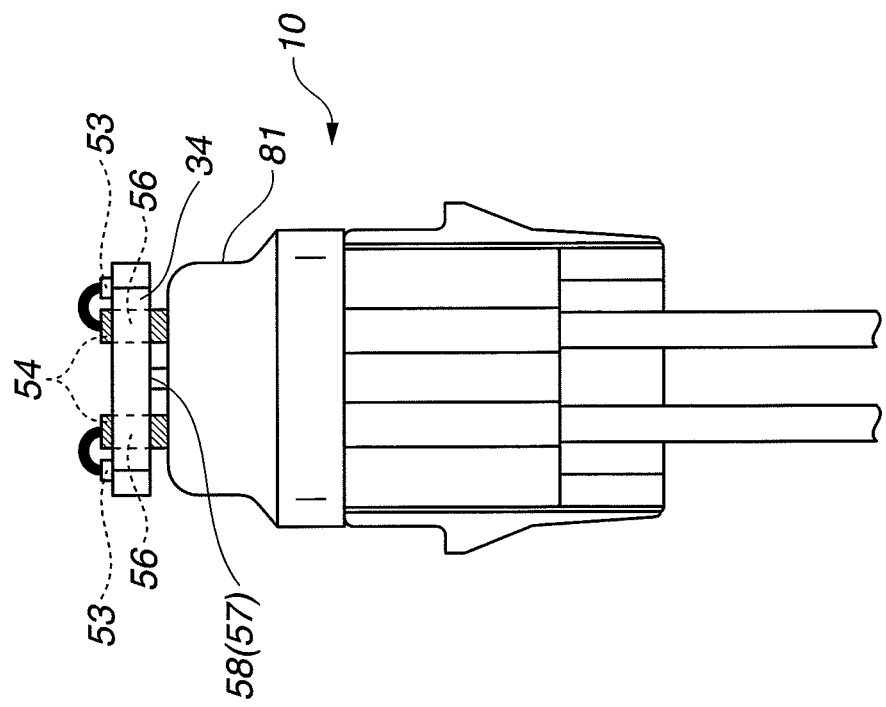
FIG. 10A is a view showing a first variation of the circuit section 10.
Figure 10B:
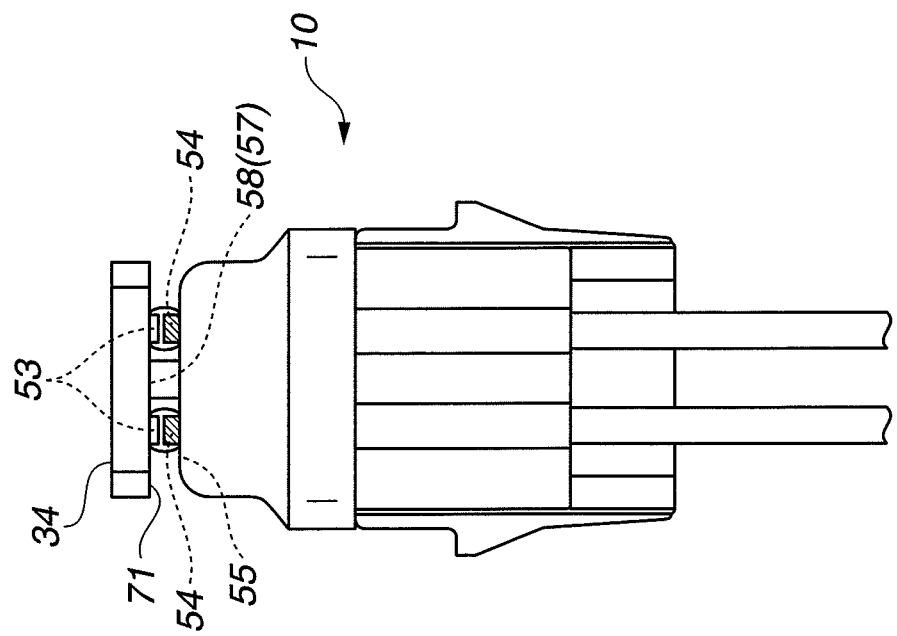
FIG. 10B is a view showing a second variable of the circuit section 10.

<VARIATIONS> Although the invention has been described above with reference to certain embodiments of the invention, the invention is not limited to the embodiments described above. Various modifications and variations of the embodiments described above are possible within the purview of the present invention. For example, FIGS. 10A and 10B show two variations of the circuit section 10. FIG. 10A shows a first variation of the circuit section 10 in the state before the formation of seal portion 36. FIG. 10B shows a second variation of the circuit section 10 in the state before the formation of seal portion 36. In FIGS. 10A and 10B, terminal portions 54 are shown by hatching.

In the gas sensor 2 of the example shown in FIG. 7, the connection portion 53 is formed around the through holes 56 in the second board surface 72. However, the connection portion 34 is not limited to this arrangement, but the connection portion 34 may be formed in or on at least one of first and second board surfaces 71 and 72.

In the example shown in FIG. 10A, the connection portion 53 (or the at least one connection portion 54) is formed in or on the first board surface 71 facing to the mount surface 55. The connection portion 53 is joined (or fastened) with the corresponding terminal portion 54 projecting from mount surface 55 in the state in which circuit board 34 is supported on the support surface 34 of at least one support projection 57. In this case, the circuit board 34 may be so formed that there is no through hole 56, and the terminal portion 54 does not extend through circuit board 34.

In the example of the first embodiment, and the variation shown in FIG. 10A, the circuit board 34 is fixed to the support projection 57 by fastening the connection portion 53 of circuit board 34 to the terminal portion 54. However, this arrangement is not limitative, but it is possible to employ other arrangements such as an arrangement in which circuit board 34 is not fixed to the support surface 58 of support projection 57.

In the example shown in FIG. 10B, the terminal portion 54 inserted through the through hole 56 is connected with the connection portion 53 of circuit board 34 by wire connection or wire bonding in the state in which the circuit board 34 is supported on the support surface 58 of support projection 57 above the mount surface 55.

Circuit board 34 and first circumferential side surface 81 are buried in the thermoplastic resin of seal portion 36 in the illustrated examples. However, this arrangement is not limitative, but it is optional to employ various other forms of the seal portion as long as circuit board 34 is enclosed (tightly) in the seal portion.

In the example shown in FIG. 7, two of the support projections 57 are formed, respectively, in two (half) regions into which the area of the mount surface 55 is divided. However, this arrangement is not limitative, but it is possible to employ an arrangement in which only one support projection 57 is formed in the mount surface 55 or an arrangement in which a plurality of support projections 57 are distributed adequately or arranged symmetrically around a center of the mount surface 55. Furthermore, the terminal portion 54 may be shaped in the columnar shape or in various other shapes.

Storage medium 33 is mounted on the second (upper) board surface 72 of circuit board 34 in the example shown in FIG. 7. However, this arrangement is not limitative, but it is possible to employ an arrangement in which storage medium 33 is mounted on the first (lower) board surface 71. Moreover, the gas sensor is not limited to the NOx sensor. For example, the gas sensor 2 may be an oxygen sensor for sensing an oxygen concentration in a measurement gas such as exhaust gas, or may be a full range or wide range air-fuel ratio sensor.

The stopper surface 67 of stopper projection 66 of output base 19 (case portion 49) may be substantially perpendicular to the side surface of case portion 49, or may be inclined so that an angle formed with the side surface of case portion 49 is equal to an angle such as an acute angle.

The individual information stored in storage medium 33 may be information to be used for the output correction for correcting or modifying the output of sensing element 4, or may be information used for drive correction or modification of sensing element 4. For example, in the configuration performing an electricity supplying control (heating control) of the heater 9 so as to bring the resistance of heater 9 to a desired value, the individual information may include individual data on the value of resistance (impedance) of heater 9 of the corresponding gas sensor, and the desired value may be corrected in accordance with the individual data. In the configuration controlling the supply of electricity to heater 9 so as to bring the internal resistance (impedance) of a cell of the sensing element 4 (the oxygen partial pressure sensing cell 12, for example) to a desired target value, the individual information may include individual data on the value of internal resistance of the cell of the sensing element of the corresponding gas sensor. In this case, the correction may be performed so as to correct the desired value in accordance with the individual data, or to correct a periodically sensed actual internal resistance of the cell.

According to the illustrated embodiments of the present invention, a gas sensing apparatus can have the following features basically. X1) A gas sensing apparatus comprising: a sensing element for sensing a gas component in a gas; a storage medium to store individual information prepared individually for the sensing element (for use in control of the sensing element, for example); a circuit board supporting the storage medium; a seal portion of a resin covering the circuit board; and an output base including a mount surface facing to the circuit board, and a support projection projecting from the mount surface and supporting the circuit board.

According to the illustrated embodiments of the present invention, the gas sensing apparatus as recited in X1 may further have at least one (any one or more) of the following features. X2) The apparatus as recited in X1, wherein the support projection forms a clearance between the circuit board and the mount surface. X3) The apparatus as recited in at least one of X1 and X2, wherein the clearance is filled with the resin of the seal portion. X4) The apparatus as recited in at least one of X1~X3, wherein the apparatus further comprises a terminal portion projecting from the mount surface of the output base and including a portion connected with the circuit board, to deliver the individual information from the storage medium through the circuit board.

X5) The apparatus as recited in at least one of X1~X4, wherein the output base includes a base portion including a larger portion having an outer circumferential side surface and a smaller portion having an inner circumferential side surface, projecting from the larger portion toward the circuit board, and including the mount surface facing to the circuit board, the inner circumferential side surface of the smaller portion is buried in the resin of the seal portion whereas the outer circumferential side surface of the larger portion is bared without being buried in the resin of the seal portion. X6) The apparatus as recited in at least one of X1~X5, wherein the output base is made of a resin, and the seal portion is made of the resin having a thermal expansion coefficient higher than that of the resin of the output base. X7) The apparatus as recited in at least one of X1~X6, wherein the seal portion includes a domed portion bulging from the output base, covering (or embedding) the circuit board and the storage medium, and including a top surface and an outside circumferential surface which are bared (so that thermal expansion of the seal portion is not restricted).

X8) The apparatus as recited in at least one of X1~X7, wherein the apparatus further comprises a connector adapted to connect the circuit board and the sensing element to an external device (such as the sensor control device 3). X9) The apparatus as recited in X8 wherein the output base includes a base portion to support the circuit board and the seal portion, a case portion enclosing an information line (or second wiring section) connecting the connector with the storage medium through the circuit board, and a holding or holder portion connected with the connector. X10) The apparatus as recited at least one of X8 and X9, wherein the apparatus further comprises a bracket connecting the holding portion of the output base with the connector. X11) The apparatus as recited in X10, wherein the bracket is a plate member including a hook portion interlocked (or engaged) with the holding portion of the output base by elastic deformation of the hook portion. X12) The apparatus as recited in at lest one of X10 and X11, wherein the bracket is made of a metallic material. X13) The apparatus as recited in at lest one of X10~X12, wherein the bracket is a flat plate. X14) The apparatus as recited in at least one of X8~X13, wherein the seal portion bulges from the output base toward the connector.

X15) The apparatus as recited in at least one of X9~X14, wherein the information line includes at least one lead line. X16) The apparatus as recited in at least one of X9~X15, wherein the information line includes a first segment extending from the output base in a first direction away from the connector, a second segment extending from the connector in the first direction over the seal portion, and a U-shaped segment connecting the first segment and the second segment so as to form a continuous line connecting the circuit board with the connector.

X17) The apparatus as recited in at least one of X1~X16, wherein the apparatus further comprise an elastic member enclosing the output base and the seal portion. X18) The apparatus as recited in X17, wherein the elastic member further encloses an (or the) information line (or second wiring section) connecting a (or the) connector with the circuit board, and a signal line (or first wiring section) connecting the connector with the sensing element. The information line may include at least one lead line (52), and the signal line may include at least one lead line (51). X19) The apparatus as recited in X18, wherein the elastic member is a tubular member including a first open end (74) through which the signal line extends to the sensing element, a second open end (68) enclosing the information line and the signal line which extending to the connector, and an intermediate portion (69) enclosing the output base and the seal portion. X20) The apparatus as recited in X19, wherein the elastic member encloses a (or the) bracket connecting the output base with the connector and extending through the second open end of the elastic member to the connector. X21) The apparatus as recited in at least one of X19 and X20, wherein the second open end includes an opening which is greater than an opening of the first open end, and which is adapted to insert the output base into the elastic member from the second open end.

X22) The apparatus as recited in at least one of X17~X21, wherein the output base includes a side wall surface formed with a lateral (stopper) projection, and the elastic member includes an inside surface formed with an inside groove engaging with the lateral projection of the output base. X23) The apparatus as recited in at least one of X17~X22, wherein the lateral projection of the output base is shaped to engage with the inside groove of the elastic member and to prevent extraction of the elastic member from the output base.

X24) The apparatus as recited in at least one of X1~X23, wherein the circuit board includes a connection portion joined with a terminal portion in a state in which the circuit board is supported by the support projection and wherein the seal portion is a member of a thermoplastic resin formed around the circuit board so as to bury the circuit board in the seal portion in a state in which the terminal portion is joined with the connection portion.

X25) The apparatus as recited in at least one of X1~X24, the apparatus comprises a gas sensor comprising the sensing element, the storage medium, the circuit board, the seal portion and the output base. X26) The apparatus as recited in X25, wherein the apparatus further comprises a sensor control section electrically connected with the gas sensor.

X26) The apparatus as recited in at least one of X1~X25, wherein the seal portion includes an underlying portion supported by the output base, and a head portion bulging from the underlying portion of the seal portion in the direction in which the mount surface faces, to a top end of the seal portion, embedding the circuit board and the storage medium, the seal portion being supported only at the underlying portion so that the head portion being free.

This application is based on a prior Japanese Patent Application No. 2009-215878 filed on Sep. 17, 2009. The entire contents of this Japanese Patent Application are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor comprising:
a sensing element to output a concentration signal representing a concentration of a gas component in a gas;
a storage medium to store individual information prepared individually for the sensing element for use in control of the sensing element;
a circuit board supporting the storage medium mounted on the circuit board:
a seal portion of a resin covering the circuit board liquid-tightly;
an output base including a mount surface facing to the circuit board, and supporting a terminal portion which is connected with the circuit board and arranged to deliver the individual information through the circuit board; and
the output base including a support projection projecting from the mount surface and including a support surface supporting the circuit board,
wherein the circuit board includes a first board surface and a second board surface opposite to the first board surface, the support surface of the support projection of the output base is arranged to abut on the first board surface facing toward the mount surface of the output base, and the storage medium is mounted on the second board surface.

2. A gas sensor comprising:
a sensing element to output a concentration signal representing a concentration of a gas component in a gas to be examined;
a storage medium to store individual information prepared individually for the sensing element for use in at least one of an output correction and a drive correction of the sensing element;
a circuit board supporting a storage medium which is mounted on a circuit board and including a connection portion electrically connected with the storage medium;
a seal portion of the resin which is a thermoplastic resin covering the circuit board liquid-tightly; and
an output base including a mount surface facing to the circuit board, and supporting a terminal portion which is connected with the circuit board, the terminal portion extending through the mount surface and being arranged to deliver the individual information from the storage medium through the connection portion of the circuit board;

the output base including a support projection projecting from the mount surface toward the circuit board and including a support surface supporting the circuit board in a state in which a first board surface of the circuit board faces toward the mount surface, and a second board surface of the circuit board faces away from the mount surface;

the connection portion of the circuit board being joined with the terminal portion in a state in which the circuit board is supported by the support surface of the support projection; and the seal portion being formed around the circuit board so that the circuit board is buried in the thermoplastic resin in a state in which the terminal portion is joined with the connection portion.

3. The gas sensor as recited in claim 2, wherein the circuit board includes a through hole, the terminal portion is inserted through the through hole, and the connection portion is formed around the through hole in at least one of two opposite board surfaces of the circuit board.

4. The gas sensor as recited in claim 2, wherein the gas sensor further comprises a connector adapted to connect the gas sensor with a sensor control section, and a tubular elastic member enclosing the output base and a lead line connecting the connector with the connection portion of the circuit board and including an end portion connected with the connector;

wherein the output base includes a case portion enclosing a part of the lead line, and a stopper projection projecting from a side surface of the case portion; and wherein the tubular elastic member includes an open end portion enclosing the end portion of the lead line in a state in which the output base with the seal portion is connected with the connector, and a receiving portion which is adjacent to the open end portion, which receives the output base, and which includes an inside surface formed with a groove engaging with the stopper projection of the output base received in the receiving portion.

5. A gas sensor comprising:

a sensing element to output a concentration signal representing a concentration of a gas component in a gas;

a storage medium to store individual information prepared individually for the sensing element for use in control of the sensing element;

a circuit board supporting the storage medium mounted on the circuit board a seal portion of a resin covering the circuit board liquid-tightly;

an output base including a mount surface facing to the circuit board, and supporting a terminal portion which is connected with the circuit board and arranged to deliver the individual information through the circuit board; and the output base including a support projection projecting from the mount surface and including a support surface supporting the circuit board, wherein the support projection of the output base defines a clearance between the circuit board and the mount surface of the output base, the resin of the seal portion is filled in the clearance, and the circuit board and the storage medium are embedded in the resin of the seal portion.

6. A gas sensor comprising a sensing element to output a concentration signal representing a concentration of a gas component in a gas;

a storage medium to store individual information prepared individually for the sensing element for use in control of the sensing element;

a circuit board supporting the storage medium mounted on the circuit board;

a seal portion of a resin covering the circuit board liquid-tightly:

an output base including a mount surface facing to the circuit board, and supporting a terminal portion which is connected with the circuit board and arranged to deliver the individual information through the circuit board; and the output base including a support projection projecting from the mount surface and including a support surface supporting the circuit board, wherein the output base includes a base portion which includes the mount surface facing in a first direction toward the circuit board and which supports the seal portion bulging in the first direction from the base portion and embedding the circuit board and the storage medium, and a case portion which projects from the base portion in a second direction opposite to the first direction, and which encloses a lead line extending in the second direction from the terminal portion to deliver the individual information.

7. The gas sensor as recited in claim 6 wherein the lead line includes a wire including a first segment extending in the second direction in the case portion of the output base, a second segment extending from the first segment curvedly in a form of a U-turn, and a third segment extending from the second segment in the first direction.

8. A gas sensor comprising:

a sensing element to output a concentration signal representing a concentration of a gas component in a gas;

a storage medium to store individual prepared individually for the sensing element for se in control of the sensing element;

a circuit board supporting the storage medium mounted on the circuit board;

a seal portion of a resin covering the circuit board liquid-tightly;

an output base including a mount surface facing to the circuit board, and supporting a terminal portion which is connected with the circuit board and arranged to deliver the individual information through the circuit board; and the output base including a support projection projecting from the mount surface and including a support supporting the circuit board, wherein the gas sensor further comprises a connector adapted to connect the gas sensor with a sensor control section, a first wiring section including at least one first lead line electrically connecting the sensing element to the connector and a second wiring section including at least one second lead line electrically connecting the circuit board with the connector to deliver the individual information from the storage medium to the sensor control section through the connector, the output base is connected with the connector by a bracket, and the output base includes a base portion including the mount surface facing toward the connector and an opposite surface facing away from the connector, and a case portion which encloses the second wiring section connected with the terminal portion, and which projects from the opposite surface of the base portion in a direction away from the connector.

9. The gas sensor as recited in claim 8, wherein the gas sensor further comprises a tubular elastic member including a first tube end portion facing to the connector and enclosing the first and second wiring sections extending through the first tube end portion to the connector, an intermediate tube portion enclosing the output base and the circuit board, and a second tube end portion enclosing the first wiring section extending through the second tube end portion to the sensing element.

* * * * *